US00PP34287P2

(12) United States Plant Patent
O'Connell

(10) Patent No.: US PP34,287 P2
(45) Date of Patent: May 31, 2022

(54) ***ECHEVERIA* PLANT NAMED 'FAIRY PRINCESS'**

(50) Latin Name: ***Echeveria* hybrid**
Varietal Denomination: Fairy Princess

(71) Applicant: Altman Specialty Plants, Inc, Vista, CA (US)

(72) Inventor: Renee O'Connell, Escondido, CA (US)

(73) Assignee: Altman Specialty Plants Inc., Vista, CA (US)

( * ) Notice: Subject to any disclaimer, the term of this patent is extended or adjusted under 35 U.S.C. 154(b) by 0 days.

(21) Appl. No.: 17/357,604

(22) Filed: Jun. 24, 2021

(51) Int. Cl.
*A01H 6/12* (2018.01)
*A01H 6/32* (2018.01)

(52) U.S. Cl.
USPC ..... Plt./373
CPC ..... *A01H 6/32* (2018.05)

(58) Field of Classification Search
USPC ..... Plt./373
CPC ..... A01H 6/32
See application file for complete search history.

(56) References Cited

U.S. PATENT DOCUMENTS

PP29,312 P3 * 5/2018 van Langen ..... A01H 5/12 Plt./373
PP29,758 P3 * 10/2018 Ammerlaan ..... A01H 5/12 Plt./373
PP30,005 P2 * 12/2018 Ammerlaan ..... A01H 6/00 Plt./373
PP30,037 P2 * 12/2018 O'Connell ..... A01H 5/12 Plt./373
PP30,373 P3 * 4/2019 van Langen ..... A01H 5/12 Plt./373
PP31,493 P3 * 2/2020 van Langen ..... A01H 5/12 Plt./373

* cited by examiner

*Primary Examiner* — Anne Marie Grunberg
(74) *Attorney, Agent, or Firm* — Cassandra Bright

(57) ABSTRACT

A new and distinct variety of *Echeveria* hybrid plant named 'Fairy Princess' is disclosed, characterized by rosettes of rose-violet with margins of a lighter color. Plants grow quickly and robustly. *Echeveria* 'Fairy Princess' does not seem to be afflicted with many of the fungal and bacterial pathogens that plague other varieties of *Echeveria*. *Echeveria* is a popular genus, typically produced as container plants for the patio or as landscape plants.

4 Drawing Sheets

Latin name of the genus and species: *Echeveria* hybrid.
Variety denomination: 'FAIRY PRINCESS'.

BACKGROUND OF THE INVENTION

The new cultivar, *Echeveria* 'Fairy Princess', is the product of chance discovery. The new variety was selected as a naturally occurring whole plant mutation of the unpatented parent variety *Echeveria hybrida* cultivar 'Perle von Nurnberg'. The discovery was made during April of 2017, in Vista, Calif., at a commercial greenhouse.

Asexual reproduction of the new cultivar 'Fairy Princess' vas first performed in Vista, Calif., at a commercial greenhouse, by vegetative offsets in May of 2017. *Echeveria* 'Fairy Princess' has since produced at least 17 generations and has shown that the unique features of this cultivar are stable and reproduced true to type.

SUMMARY OF THE INVENTION

The cultivar 'Fairy Princess' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'FAIRY PRINCESS'. These characteristics in combination distinguish 'FAIRY PRINCESS' as a new and distinct *Echeveria* cultivar:

1. *Echeveria* 'Fairy Princess' forms rosettes comprised of rose-violet leaves with lighter margins, as compared to many other *Echeverias* displaying rosettes of pale blue, blue-green or shades of green.
2. *Echeveria* 'Fairy Princess' is a fast and robust grower, enhancing production times in a commercial nursery.
3. *Echeveria* 'Fairy Princess' does not seem to be afflicted with many of the fungal and bacterial pathogens that plague other varieties of *Echeveria*.

PARENTAL COMPARISON

Plants of the new cultivar 'Fairy Princess' are similar to plants of the parent in most horticultural characteristics. However, plants of the new cultivar 'Fairy Princess' differ in the following:

1. *Echeveria* 'Fairy Princess' forms rosettes with longer leaves than does *Echeveria* 'Perle von Nurnberg'.
2. *Echeveria* 'Fairy Princess' often exhibits rosettes with more undulate leaves than does *Echeveria* 'Perle von Nurnberg', sometimes giving the entire rosette and more wavy or undulate appearance.
3. *Echeveria* 'Fairy Princess' has a similar growth rate as *Echeveria* 'Perle von Nurnberg'.

4. *Echeveria* 'Fairy Princess', exhibits the same intense rose violet coloration as *Echeveria* 'Perle von Nurnberg'.

COMMERCIAL COMPARISON

The new cultivar 'Fairy Princess' can be compared to *Echeveria* 'Arctic Ice', U.S. Plant Pat. No. 29,584. Plants of the new cultivar 'Fairy Princess' differ in the following:

1. *Echeveria* 'Fairy Princess' produces rose violet rosettes, whereas *Echeveria* 'Arctic Ice' produces greyed-green rosettes with a strong glaucous covering.
2. *Echeveria* 'Fairy Princess' produces larger foliage than 'Arctic Ice'.
3. Plants of 'Arctic Ice' are denser, having 80 to 100 leaves per rosette, compared to the 35 to 50 leaves found on a typical rosette of 'Fairy Princess'.

The new cultivar 'Fairy Princess' can be compared to the commercially known, unpatented *Echeveria agavoides* 'Lipstick'. Plants of the new cultivar 'Fairy Princess' are similar to *Echeveria agavoides* 'Lipstick' in most horticultural characteristics. However, plants of the new cultivar 'Fairy Princess' differ in the following:

1. *Echeveria* 'Fairy Princess' produces rose violet rosettes, whereas *Echeveria agavoides* 'Lipstick' produces lime to frosty green rosettes with burgundy apices.
2. *Echeveria* 'Fairy Princess' exhibits a faster growth rate than does *Echeveria agavoides* 'Lipstick', enhancing crop times in a production nursery environment.
3. *Echeveria* 'Fairy Princess' displays an accentuating leaf margin that is lighter in color than the main color of the leaf, whereas *Echeveria agavoides* 'Lipstick' exhibits a darker leaf margin.
4. *Echeveria* 'Fairy Princess' forms loose rosettes of somewhat undulate rose violet leaves, whereas *Echeveria agavoides* 'Lipstick' produces rosettes of rigid, pointed leaves.
5. The leaves of the rosettes of *Echeveria* 'Fairy Princess' are somewhat glaucous and not particularly fleshy, whereas the leaves of *Echeveria agavoides* 'Lipstick' are not glaucous and are often quite fleshy.

BRIEF DESCRIPTION OF THE PHOTOGRAPHS

The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of new *Echeveria* 'Fairy Princess'.

DETAILED BOTANICAL DESCRIPTION

Figure 1:
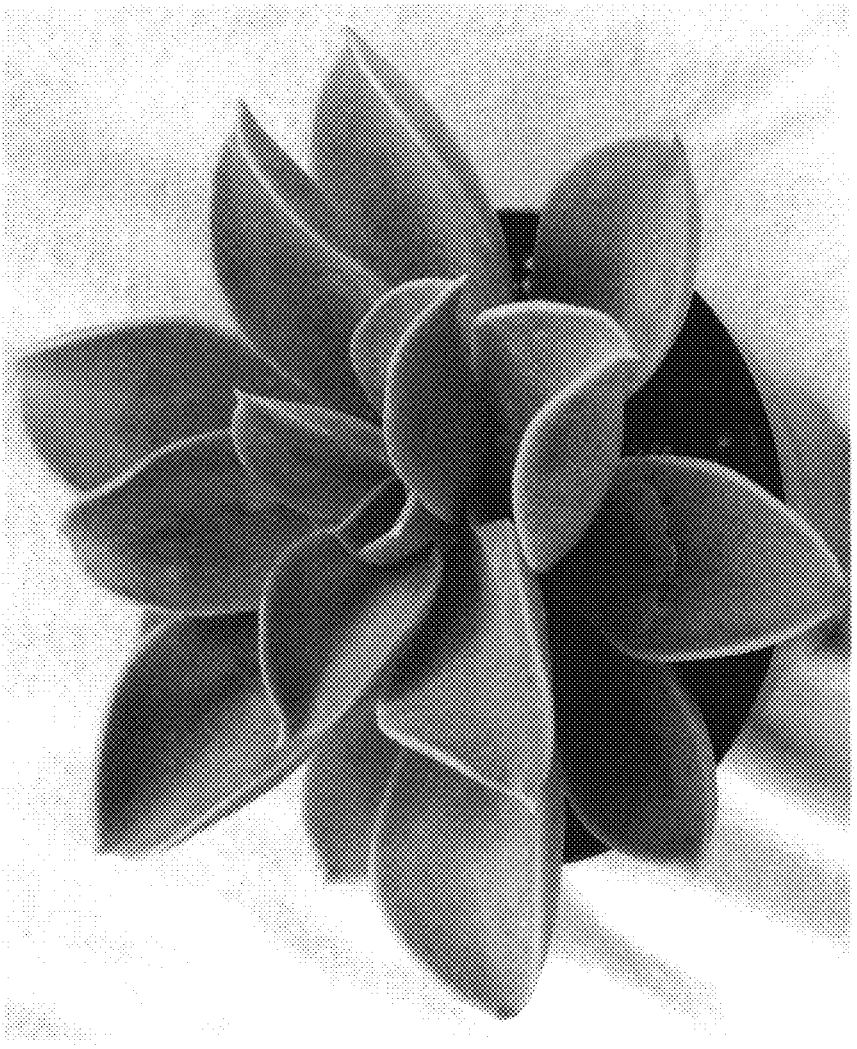
FIG. 1 illustrates in full color a plant of *Echeveria* 'Fairy Princess' grown in a greenhouse (approximately 2500 foot candles) in Vista, Calif. This plant is approximately 3 months old from a rooted cutting.
Figure 2:
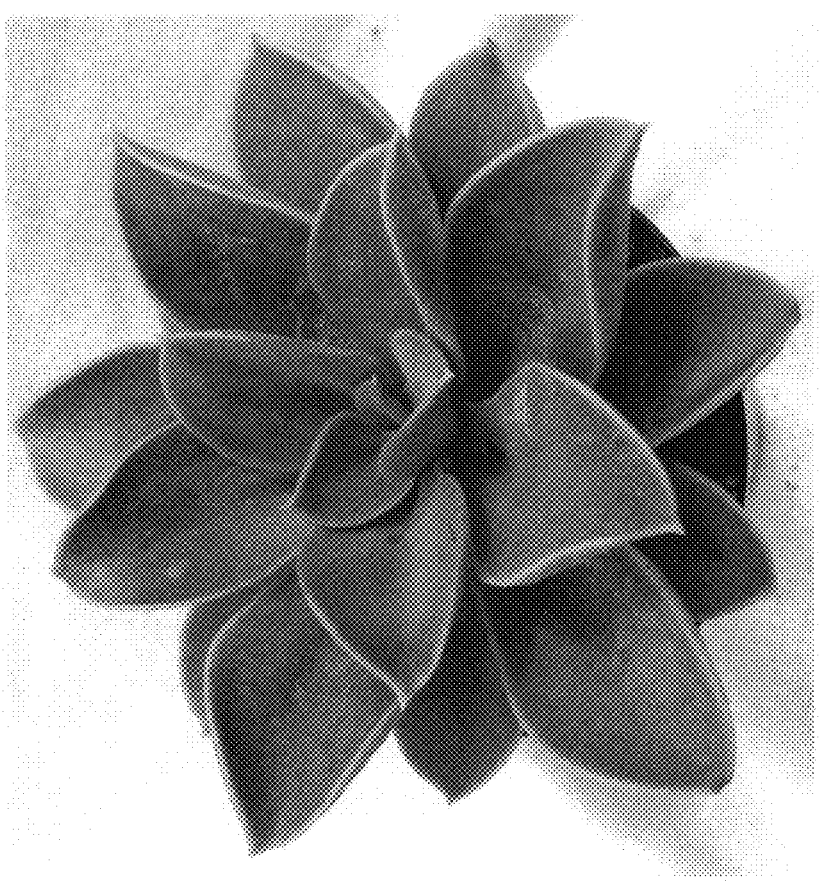
FIG. 2 illustrates in full color the rosette from the same plant as FIG. 1 from a different angle.
Figure 3:
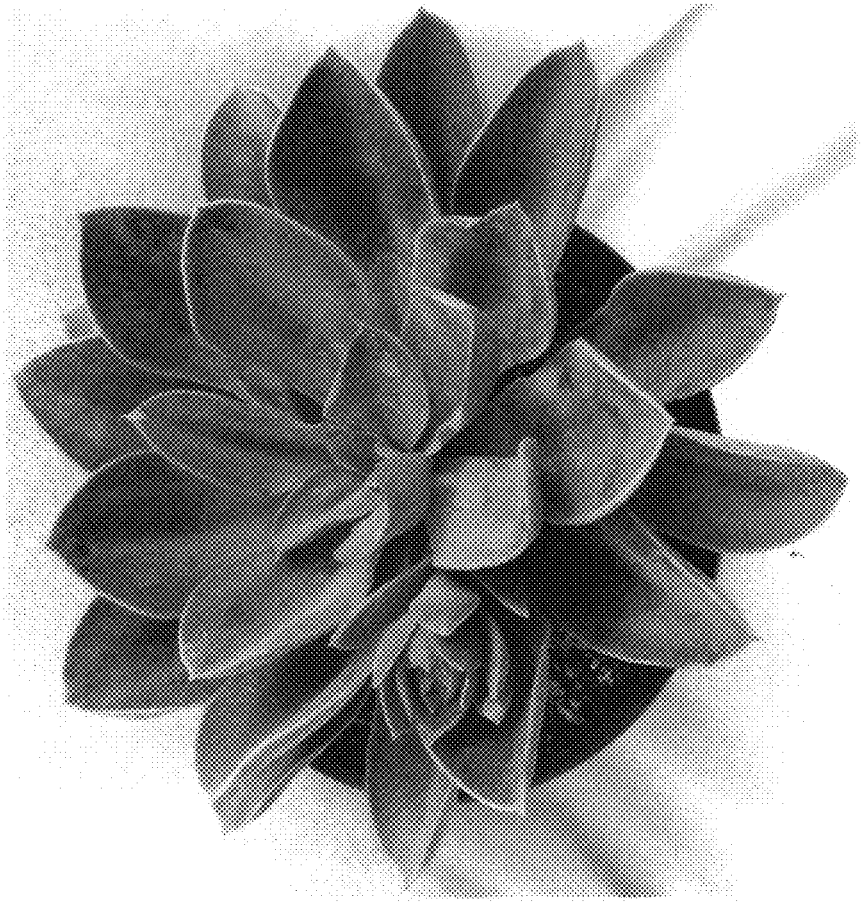
FIG. 3 illustrates in full color the rosette of an older *Echeveria* 'Fairy Princess' (about 6 months), grown in a greenhouse (approximately 2500 foot candles) in Vista, Calif.
Figure 4:
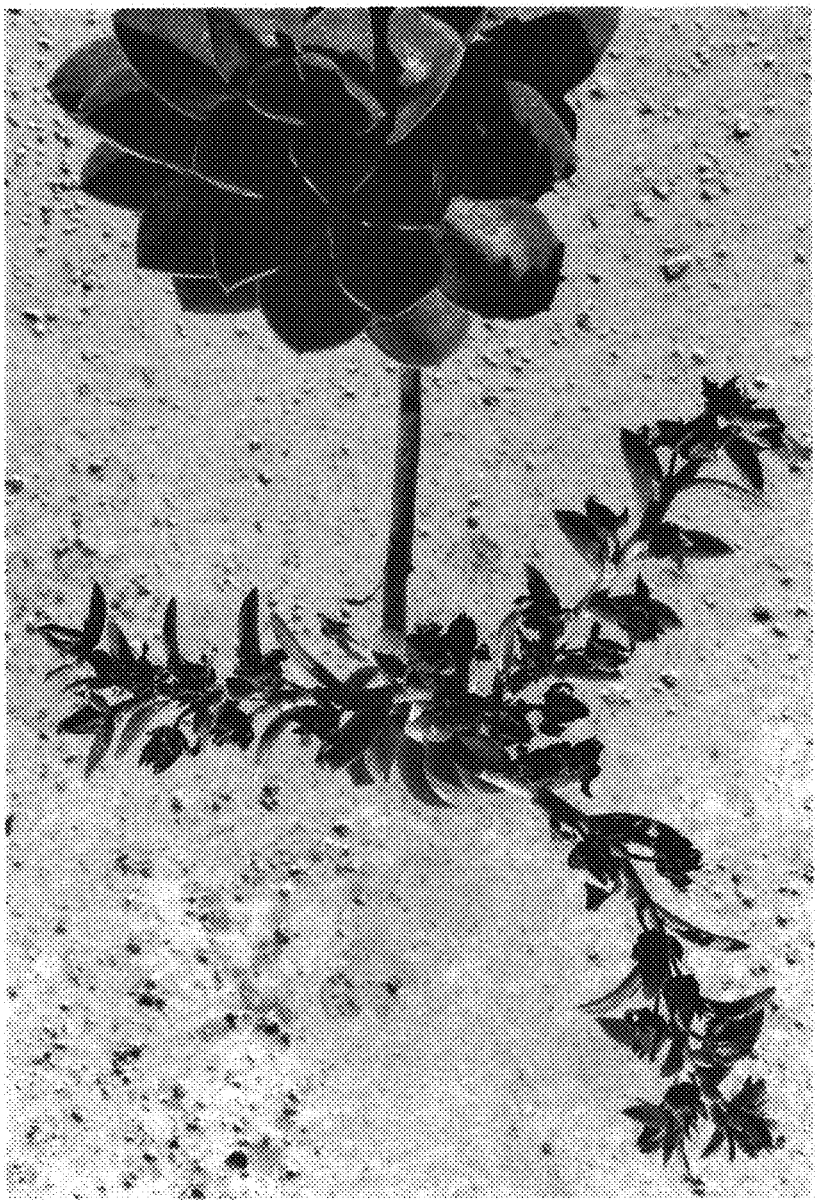
FIG. 4 illustrates in full color an aging inflorescence of *Echeveria* 'Fairy Princess'. Individual flowers are spent, however the typical formation of the inflorescence can be seen.

In the following description, color references are made to The Royal Horticultural Society Colour Chart, 2007, except where general terms of ordinary dictionary significance are used. The following observations and measurements describe 'Fairy Princess' plants grown in a commercial nursery in Vista, Calif. Temperatures ranged from about 2° C. to 38° C. night and day. No artificial light, photoperiodic treatments or chemical treatments were given to the plants. Natural light conditions were approximately 2500 fc of light. Measurements and numerical values represent averages of typical plant types.

Botanical classification: *Echeveria* hybrid 'Fairy Princess'.

PROPAGATION

Type of propagation typically used: Terminal vegetative cuttings.

Time to initiate roots: About 11 days at approximately 24° C.

Root description: Fibrous, brown, not accurately measured with R.H.S. chart.

PLANT

Age of plant described: Approximately 4 months from a cutting.

Container size of the plant described: 1 gallon.

Growth habit: Densely and somewhat flattened rosulate plant.

Height: Approximately 12 cm to top of highest leaf. Approximately 15 cm to 25 cm to top of highest inflorescence.

Plant spread: Approximately 20.0 cm.

Growth rate: Rapid.

Branching characteristics: Not typically observed.

FOLIAGE

Leaf:

*Arrangement*.—Rosulate.

*Average length*.—Average range 6.5 to 9 cm.

*Average width at widest*.—3.5 cm.

*Width at base*.—Average 1.2 cm.

*Thickness of leaf*.—Thickest section about 6 mm.

*Shape of blade*.—Spatulate.

*Apex*.—Broad acute, with a single, small mucronate tip, approximately 2 to 3 mm long.

*Base*.—Broad attenuate.

*Margin*.—Entire.

*Texture of top surface*.—Glaucous.

*Texture of bottom surface*.—Glaucous.

*Appearance of top surface*.—Matte.

*Appearance of bottom surface*.—Matte.

*Quantity of leaves per plant*.—Average range 35 to 50.

*Color*.—Young foliage upper side: Near RHS Greyed-Purple N187B flushed Red 53D. Strong margin coloration near Red 52A, 52B and Yellow 10B. Glaucous layer over entire surface colored near Greyed-Purple N187C. Young foliage under side:

Near RHS Greyed-Purple 185B flushed Red 53D. Strong margin coloration near Red 55D. Glaucous layer over entire surface colored near Greyed-Purple N187C. Mature foliage upper side: Near RHS Greyed-Red 181D. Strong margin coloration near Red 55D and Yellow 10C. Glaucous layer over entire surface colored near Greyed-Purple N187C. Mature foliage, under side: Near RHS Greyed-Red 181C. Strong margin coloration near Red 55D and Yellow 10C. Glaucous layer over entire surface colored near Greyed-Purple N187C.

FLOWER

Natural flowering season: Spring through Summer.

Inflorescence type and habit: Arching, composed of several simple or bifurcate cincinni, each cincinnus typically with 12 to 20 flowers and buds.

Rate of flower opening: About 7 to 14 days from bud stage to open flower, depending on environmental conditions.

Flower longevity on plant: 7 to 16 days, depending upon ambient temperatures.

Total inflorescence size:

*Height*.—Approximately 20 to 30 cm.

*Width*.—Approximately 16 cm.

Corolla:

*Arrangement*.—Pentagonal, fused.

*Size*.—Length: Approximately 1.5 cm. Width: Approximately 1.0 cm at widest point. Lobe Length: Approximately 5 mm. Lobe width: Approximately 4 mm.

*Petals*.—Margin: Entire. Shape: Unfused section deltate. Apex: Acute. Base: Fused, approximately ¾ entire length. Texture: Glabrous Color: When opening: Petal color, outer surface: Near Red 42A. Base near Orange-Red 32D. Inner surface: Near Yellow 10B. Apex near Red 40B. Fully opened: Outer surface: Near Red 41A. Base near Orange-Red 32D. Inner surface: Near Yellow 10B. Apex near Red 40B.

Bud: (Near opening).

*Shape*.—Conical.

*Length*.—Approximately 7 mm.

*Diameter*.—Approximately 7 mm.

*Color*.—Near Red 48C, apex 47C.

Sepals:

*Length*.—10 mm.

*Width*.—5 mm.

*Margin*.—Entire.

*Shape*.—Deltoid.

*Apex*.—Acute.

*Base*.—Truncate.

*Texture*.—Glabrous, upper and lower surfaces.

*Appearance*.—Matte upper surface, slightly glossy lower surfaces.

*Color*.—Upper: Near RHS Greyed-Purple N187A. Margin near Red 53B. Lower: Near RHS Greyed-Purple 187A. Margin near Red 53B.

Peduncle:

*Length*.—Average range 12 to 16 cm.

*Width*.—Approximately 7 mm.

*Strength*.—Strong.

*Texture*.—Glabrous.

*Color*.—Near RHS Greyed-Red 182D with glaucous layer Greyed-Purple N187D.

Pedicels:

*Length*.—Approximately 3 mm.

*Width*.—Approximately 2 mm.

*Strength*.—Strong, flexible.

*Texture*.—Glabrous.

*Color*.—Near RHS Greyed-purple 184C.

Fragrance: None detected.

REPRODUCTIVE ORGANS

Stamens: (Androecium).

*Number*.—Average 10.

*Filament length*.—Approximately 4 mm.

*Filament color*.—Near RHS Yellow 2D.

*Anther length*.—1 mm.

*Anther color*.—Near RHS Yellow 10B.

*Anther shape*.—Oblong.

*Pollen color*.—Near RHS Yellow 10B.

*Pollen quantity: Scant.*

Pistil: (Gynoecium).

*Number*.—Average 5.

*Length*.—Approximately 9 mm.

*Style color*.—Near RHS Yellow 2D.

*Stigma*.—Shape: Linear. Color: Near RHS Greyed-Red 184A. Ovary Color: Near RHS White 155C.

OTHER CHARACTERISTICS

Fruits and seeds: Seed formation not observed.

Temperature tolerance: Tolerates temperatures from approximately −2° C. to at least 35° C.

Disease/pest resistance: *Echeveria* 'Fairy Princess' does not seem to be afflicted with many of the fungal and bacterial pathogens that plague other varieties of *Echeveria*. Neither resistance or susceptibility to other normal pests of *Echeveria* has been observed.

What is claimed is:

1. A new and distinct cultivar of *Echeveria* plant named 'FAIRY PRINCESS' as herein illustrated and described.

* * * * *